(12) United States Patent
Takahashi et al.

(10) Patent No.: US 7,853,106 B2
(45) Date of Patent: Dec. 14, 2010

(54) ENDOSCOPE SYSTEM

(75) Inventors: Tadashi Takahashi, Saitama (JP);
Nobuhiro Tani, Tokyo (JP)

(73) Assignee: Hoya Corporation, Tokyo (JP)

( * ) Notice: Subject to any disclaimer, the term of this patent is extended or adjusted under 35 U.S.C. 154(b) by 0 days.

(21) Appl. No.: 11/736,792

(22) Filed: Apr. 18, 2007

(65) Prior Publication Data

US 2007/0274649 A1    Nov. 29, 2007

(30) Foreign Application Priority Data

Apr. 27, 2006    (JP)    ............... P2006-124129

(51) Int. Cl.
*G02B 6/06*    (2006.01)
*A61B 1/06*    (2006.01)

(52) U.S. Cl. ..................... 385/117; 600/180

(58) Field of Classification Search .......... 385/117; 600/180

See application file for complete search history.

(56) References Cited

U.S. PATENT DOCUMENTS

| | | | | |
|---|---|---|---|---|
| 5,184,159 A * | 2/1993 | Furuya et al. | ............... | 396/17 |
| 5,277,172 A * | 1/1994 | Sugimoto | ............... | 600/180 |
| 5,331,949 A * | 7/1994 | Funakoshi et al. | ............ | 600/109 |
| 5,984,862 A * | 11/1999 | Honda et al. | ............... | 600/180 |
| RE36,582 E * | 2/2000 | Furuya et al. | ............... | 396/17 |
| 6,063,023 A * | 5/2000 | Sakiyama et al. | ............ | 600/118 |
| 6,126,593 A * | 10/2000 | Honda et al. | ............... | 600/180 |
| 6,231,504 B1 * | 5/2001 | Honda et al. | ............... | 600/180 |
| 6,261,228 B1 * | 7/2001 | Honda et al. | ............... | 600/180 |
| 6,299,577 B1 * | 10/2001 | Honda et al. | ............... | 600/180 |
| 6,319,198 B1 * | 11/2001 | Takahashi | ............... | 600/180 |
| 6,328,692 B1 * | 12/2001 | Honda et al. | ............... | 600/180 |
| 6,524,236 B2 | 2/2003 | Honda et al. | | |
| 6,545,703 B1 * | 4/2003 | Takahashi et al. | ............ | 348/69 |
| 6,980,227 B2 * | 12/2005 | Iida et al. | ............... | 348/69 |
| 7,232,410 B2 * | 6/2007 | Takahashi | ............... | 600/180 |
| 2001/0029318 A1 * | 10/2001 | Honda et al. | ............ | 600/180 |
| 2003/0076411 A1 * | 4/2003 | Iida et al. | ............... | 348/65 |
| 2003/0142205 A1 * | 7/2003 | Takahashi et al. | ............ | 348/65 |
| 2003/0160865 A1 * | 8/2003 | Takahashi | ............... | 348/65 |

(Continued)

FOREIGN PATENT DOCUMENTS

JP    2000-075220    3/2000

(Continued)

OTHER PUBLICATIONS

English Language Abstract and English Language Computer-Generated Translation of JP 2000-075220.

(Continued)

*Primary Examiner*—Rhonda S Peace
(74) *Attorney, Agent, or Firm*—Greenblum & Bernstein P.L.C.

(57) ABSTRACT

An endoscope system comprises an electric scope and a light source apparatus. The light source apparatus has a light source and a light control apparatus. The light control apparatus adjusts a quantity of light that is incident to the electric scope, based on a comparison between a scope characteristic that indicates a relative value of the quantity of light that can be incident to the electric scope and a light source total characteristic that indicates a relative value of the quantity of the light radiated from the light source to the electric scope.

12 Claims, 11 Drawing Sheets

U.S. PATENT DOCUMENTS

| | | | |
|---|---|---|---|
| 2004/0064019 A1* | 4/2004 | Chang et al. | 600/180 |
| 2004/0122291 A1* | 6/2004 | Takahashi | 600/180 |
| 2005/0010083 A1* | 1/2005 | Iriyama | 600/180 |
| 2005/0234302 A1* | 10/2005 | MacKinnon et al. | 600/181 |
| 2007/0010712 A1 | 1/2007 | Negishi | |
| 2007/0088193 A1* | 4/2007 | Omori et al. | 600/101 |
| 2007/0149857 A1* | 6/2007 | Yabe et al. | 600/180 |

FOREIGN PATENT DOCUMENTS

| | | |
|---|---|---|
| JP | 2006-006803 | 1/2006 |
| JP | 2006-006832 | 1/2006 |

OTHER PUBLICATIONS

English Language Abstract and English Language Computer-Generated Translation of JP 2006-006803.

English Language Abstract and English Language Computer-Generated Translation of JP 2006-006832.

U.S. Appl. No. 11/736,776 to Takahashi et al., filed Apr. 18, 2007.

* cited by examiner

Fig. 9

| | PP | PL | PC | PT | P |
|---|---|---|---|---|---|
| Video processor 30A | 0.6 | 1.5 | 1.2 | 1.1 | 1.2 |
| Video processor 30B1 | 1 | 1 | 1 | 1 | 1.0 |
| Video processor 30B2 | 1 | 1.8 | 1 | 1 | 1.8 |

Fig. 10

|  | EG | | EC | | EB | |
|---|---|---|---|---|---|---|
|  | 10a | 10b | 10c | 10d | 10e | 10f |
| PS | 2.2 | 2.4 | 1.8 | 2.0 | 1.3 | 1.5 |
| PC(30A) | 1.1 | 1.2 | 1.2 | 1.3 | 0.6 | 0.7 |
| PC(30B) | 1.0 | 1.0 | 1.2 | 1.2 | 0.5 | 0.6 |

Fig. 11

| Brightness level (BM value) | Light quantity ratio | Aperture variable j |
|---|---|---|
| 10 | 1.00 | 240 |
| 9 | 0.71 | 170 |
| 8 | 0.50 | 120 |
| 7 | 0.35 | 85 |
| 6 | 0.25 | 60 |
| 5 | 0.18 | 42 |
| 4 | 0.13 | 30 |
| 3 | 0.088 | 21 |
| 2 | 0.063 | 15 |
| 1 | 0.044 | 11 |

ENDOSCOPE SYSTEM

BACKGROUND OF THE INVENTION

1. Field of the Invention

The present invention relates to an endoscope system, and in particular to an apparatus that adjusts a quantity of light that is incident to the electric scope.

2. Description of the Related Art

An apparatus that adjusts a quantity of incident light to the electric scope to prevent infection caused by an excessive illumination of light in the endoscope system, is proposed.

Japanese unexamined patent publication (KOKAI) No. 2000-75220 discloses an endoscope system that limits an aperture movement operation based on a light control signal from the electric scope.

Even though the light control operation is performed based on the information obtained by an imaging operation, a characteristic regarding the quantity of light incident to the electric scope etc. is not considered.

SUMMARY OF THE INVENTION

Therefore, an object of the present invention is to provide an endoscope system that can perform the light control operation in consideration of the quantity of light incident to the electric scope.

According to the present invention, an endoscope system comprises an electric scope and a light source apparatus. The light source apparatus has a light source and a light control apparatus. The light control apparatus adjusts a quantity of light that is incident to the electric scope based on two characteristics of the scope: a relative value of the potential quantity of light incident to the electric scope, and a relative value of the total quantity of light radiated from the light source to the electric scope.

The potential quantity of light incident to the electric scope is the maximum quantity of light in a permissible range established to prevent infection caused by an excessive illumination of light.

BRIEF DESCRIPTION OF THE DRAWINGS

The objects and advantages of the present invention will be better understood from the following description, with reference to the accompanying drawings in which:

FIG. 9 is a table that shows a relationship between the light source characteristic value, the lamp characteristic value, the combination characteristic value, the thermal characteristic value, and the relative quantity of radiated light corresponding to different kinds of video processors;

FIG. 10 is a table that shows a relationship between the scope characteristic value and the combination characteristic value corresponding to different kinds of electric scopes; and FIG. 11 is a table that shows a relationship between the brightness level, the light quantity ratio, and the aperture variable.

DESCRIPTION OF THE PREFERRED EMBODIMENTS

Figure 1:
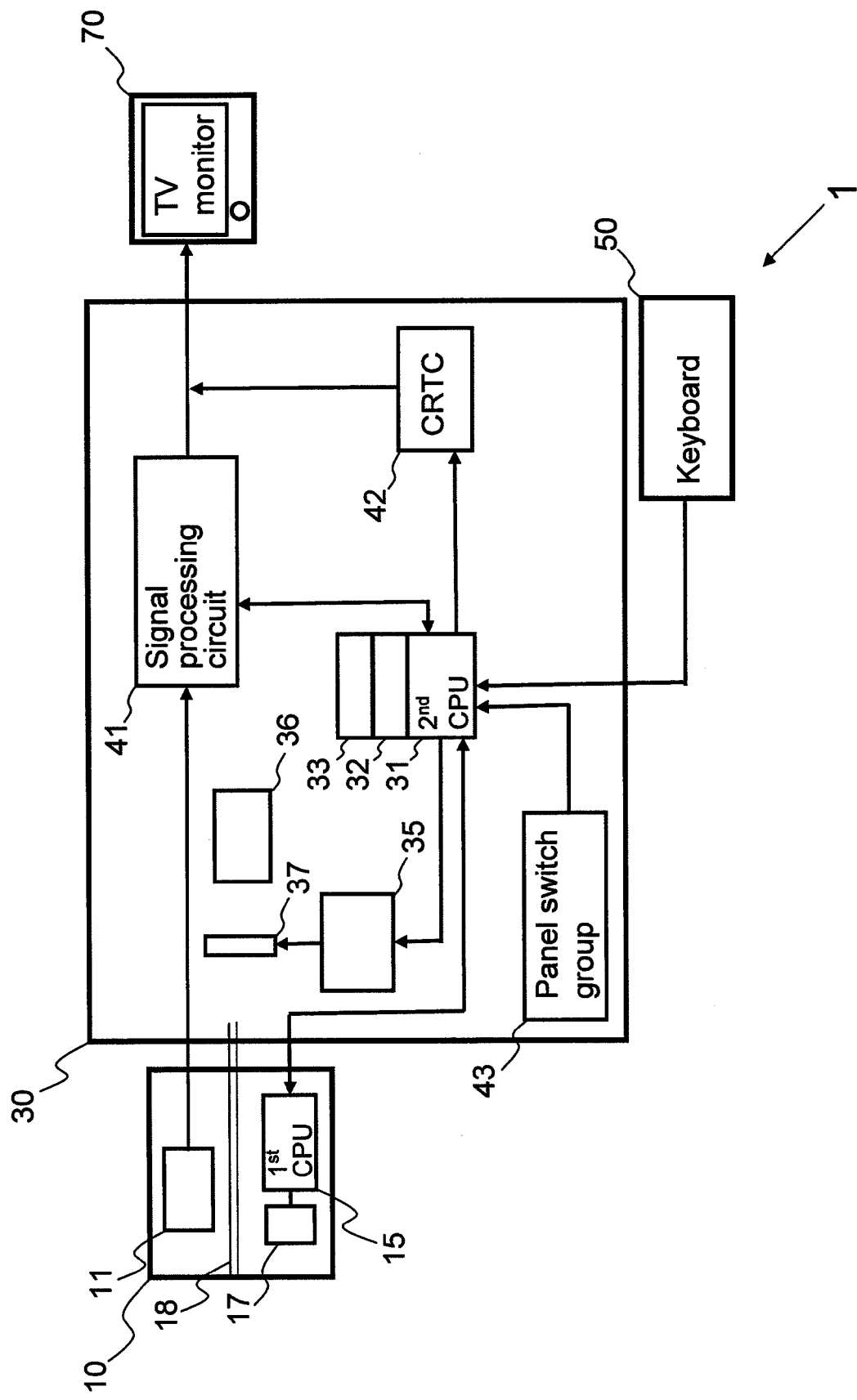
FIG. 1 is a construction diagram of the endoscope system.

The present invention is described below with reference to the embodiments shown in the drawings. As shown in FIG. 1, an endoscope system 1 in a first embodiment of the present invention is an electric endoscope apparatus and comprises an electric scope 10, a video processor 30, a keyboard 50, and a TV monitor 70.

The electric scope 10 includes an objective optical system (not depicted) and an imaging sensor 11 etc. at a tip part of the electric scope 10. The tip of the electric scope 10 is inserted into a hollow interior of an organ where a photographic subject is imaged.

The electric scope 10 has the imaging sensor 11 that is a CCD etc., an AGC (Auto Gain Controller), a video signal processing IC, a first CPU 15, and a first memory 17 (see FIG. 1). The electric scope 10 is connected to the video processor 30.

An image signal that is obtained from imaging by the imaging sensor 11 is input to the video signal processing IC through the AGC, wherefore a signal processing operation is performed on the image signal before it is output to the video processor 30. The video signal processing IC is controlled by the first CPU 15. The video signal processing IC performs a serial communication with the first CPU 15 to transmit data between each other. The video signal processing IC outputs a CCD driving signal that drives the imaging sensor 11.

The first CPU 15 is a one tip micro computer that has a ROM (Read Only Memory), a RAM (Random Access Memory), a SCI (Serial Communication Interface), and an I/O port (Input Output port). The first CPU 15 controls each part of the electric scope 10 and performs a serial communication with a second CPU 31 of the video processor 30.

The first memory 17 is a nonvolatile memory (EEPROM etc.) that is used for storing set values of each part of the electric scope 10, and is connected to the first CPU 15.

The first memory 17 stores scope characteristic value PS, which is a characteristic value of the electric scope 10 that indicates a relative quantity of the maximum permissible light incident to the electric scope 10.

The scope characteristic value PS is a relative value of a quantity of incident light that can be input to the electric scope 10 (a relative value of the potential quantity of light incident to the electric scope 10), in other words, a maximum quantity of light in a permissible range established to prevent infection otherwise caused by an excessive illumination of light.

The scope characteristic value PS is set from approximately 0.1 to 10, with consideration given to the possibility that either the incident end of the light guide 18 may be damaged by the light radiated from the light source 36, or the possibility infection caused by the excessive illumination of light emanating from the light guide 18, etc.

A large scope characteristic value PS indicates that the possibility of infection caused by the excessive illumination of light emanating from the light source 36 is low, and that the incident capacity of the electric scope 10 is large.

A small scope characteristic value PS indicates that the possibility of infection caused by the excessive illumination of light emanating from the light source 36 is high, and that the incident capacity of the electric scope 10 is small.

The scope characteristic value PS is used for calculating the aperture variable J that is described later.

In the first embodiment, the scope characteristic value PS is stored in the first memory 17 of the electric scope 10; however, it may be stored in the second memory 32 of the video processor 30. In this second configuration, a scope characteristic value PS is stored for every connected electric scope, and the scope characteristic value corresponding to the one electric scope that is connected to the video processor 30 is read out from the second memory 32 and used in the calculation of the aperture value j.

The video processor 30 has a second CPU 31, a second memory 32, an RTC (Real Time Clock) 33, a motor 35, a light source 36 that is a lamp etc., an aperture 37, a signal processing circuit 41, a CRTC (CRT controller) 42, and a panel switch group 43.

The video processor 30 converts the image signal of the photographic subject that is imaged by the electric scope 10 to a video signal that can be displayed on the TV monitor 70. The video processor 30 illuminates the photographing subject through the tip of the electric scope 10. The light from the light source 36 is radiated to the photographing subject from the tip (a radiating end part) of the electric scope 10 through a light guide 18.

The quantity of light that is radiated from the tip of the electric scope 10 to the photographing subject is automatically adjusted by the aperture control of the aperture 37 (an auto light control operation).

The second CPU 31 is a one tip micro computer that has a ROM (Read Only Memory), a RAM (Random Access Memory), an SCI (Serial Communication Interface), and an I/O port (Input Output port). The second CPU 31 controls each part of the video processor 30 and performs a serial communication with the first CPU 15 of the electric scope 10.

The RAM of the second CPU 31 temporarily stores variables such as the aperture variable J, etc., that are used for calculating the aperture control.

The signal processing circuit 41 converts the image signal that is output from the video signal processing IC of the electric scope 10, to the video signal that is displayed on the TV monitor 70. The signal processing circuit 41 outputs a luminance signal of the image signal to the second CPU 31.

The second CPU 31 controls the motor 35 that is a stepper motor, changes the aperture degree of the aperture 37, and adjusts the quantity of light to the incident end of the light guide 18; in other words, the light that is radiated to the photographing subject through the light guide 18, is adjustable.

By this adjustment of the quantity of light to the incident end of the light guide 18, either the entire amount of light radiated from the light source 36 or a portion thereof can be input to the incident end of the light guide. In the event where less than the entire amount of light radiated from the light source 36 is input to the incident end of the light guide 18, the remaining amount is not input to the incident end of the light guide 18.

The aperture degree is adjusted by changing a step of the stepper motor. The step of the stepper motor 35 is changed in proportion to the aperture variable J. Specifically, when the step of the stepper motor 35 is set to "aperture completely closed" it corresponds to 0 of the aperture variable J (J=0), on the other hand, when the step of the stepper motor 35 is set to "aperture wide open" it corresponds to 240 of the aperture variable J (J=240).

Further, the aperture variable J is proportional to the quantity of the radiated light. For example, when the quantity of light radiated to the incident end of the light guide is set to half of the quantity of light emitted from the light source 36, the aperture variable J is set to 120 (j=120).

By changing the value of the aperture variable J from 0 to 240 by the second CPU 31, the step of the stepper motor 35 is changed.

Figure 6:
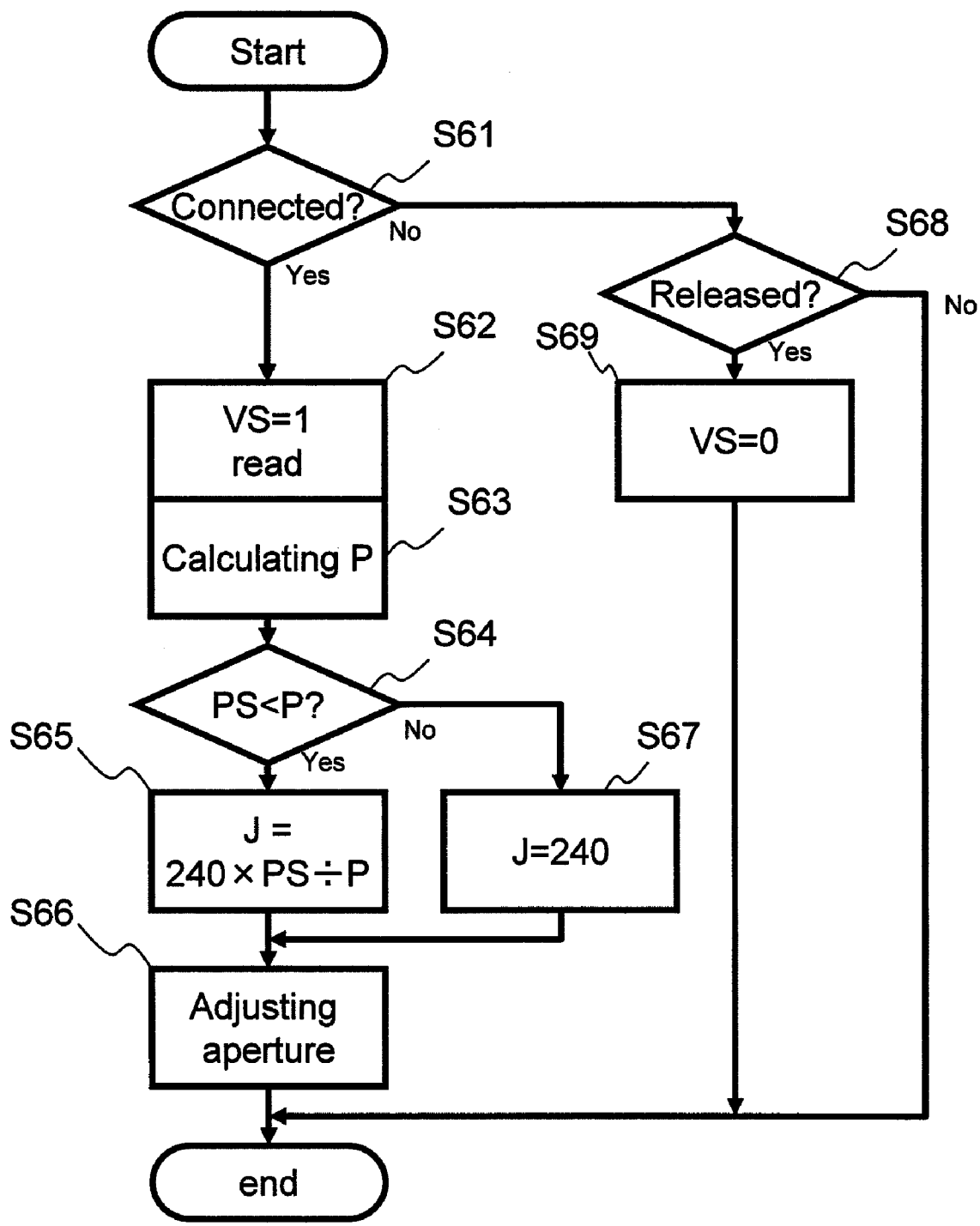
FIG. 6 is a flowchart of the confirmation operation, in detail.

Setting the value of the aperture variable J is performed by making a comparison between the scope characteristic value PS and a multiplied value P which is a product of a light source characteristic value PP, a lamp characteristic value PL, a combination characteristic value PC, and a thermal characteristic value PT (a relative light quantity of the radiated light $P=PP \times PL \times PC \times PT$, see FIG. 6).

When a key of the keyboard 50 and a switch of the panel switch group 43 are operated, the second CPU 31 performs processing operations corresponding to these operations.

The second CPU 31 reads the time and dates from the RTC 33, and indicates the time and date on the TV monitor 70 through the CRTC 42.

The second CPU 31 indicates the name of a patient, the age of the patient, the sex of the patient, and the name of a doctor etc. on the TV monitor 70 through the CRTC 42.

The second memory 32 is a nonvolatile memory (EEPROM etc.) that is used for storing set values of each part of the video processor 30, and it is connected to the second CPU 31.

The second memory 32 stores the light source characteristic value PP, the lamp characteristic value PL, the combination characteristic value PC, and the thermal characteristic value PT.

The light source characteristic value PP is a characteristic value of the light source apparatus (the video processor 30) that indicates a relative quantity of light radiated from each different kind of light source.

In the first embodiment, the light source characteristic value PP of the reference light source, which is a relative quantity of light radiated from the reference light source, is set to equal the value of 1 after a period of regular time Tc has elapsed, where the beginning of time Tc corresponds with the commencement of the use of the reference light source, and the reference light source is one of multiple light sources connected to the video processor 30.

The light source characteristic value PP is set from approximately 0.1 to 10, depending on the characteristics of the light source 36 and the video processor 30 attached thereto.

One light source is selected from among several different kinds of light sources to be the reference light source.

A large number for the light source characteristic value PP indicates that the quantity of light radiated from the light source apparatus (the video processor 30) is large.

A small number for the light source characteristic value PP indicates that the quantity of light radiated from the light source apparatus (the video processor 30) is small.

The lamp characteristic value PL is a characteristic value of the light source apparatus (the video processor 30) that indicates a change (in decreasing degree) in the quantity of light emitted from the light source 36 during a time of use t. The lamp characteristic value PL changes corresponding to the time of use t. Further, the variability in the quantity of radiated light among the same kind of the light sources (lamp) is considered to be the lamp characteristic value PL.

In the first embodiment, the lamp characteristic value PL of the reference light source, which is a relative quantity of light radiated from the reference light source, is set to equal the value of 1 after the period of regular time Tc has elapsed, where the beginning of time Tc corresponds with the commencement of the use of the reference light source.

The lamp characteristic value PL is a relative value that indicates a relative quantity of light radiated from among the same kind of light source (lamp).

The lamp characteristic value PL is set from approximately 0.3 to 4.

One light source emitting an average quantity of light from among several of the same kind of light source is selected to be the reference light source for setting the lamp characteristic value PL.

A large number for the lamp characteristic value PL indicates that the quantity of light radiated from the light source 36 is large.

A small number for the lamp characteristic value PL indicates that the quantity of light radiated from the light source 36 is small.

The regular time Tc of the light source 36 is the time that elapses from the point when the light source is set to the on state until the quantity of light radiated from the light source becomes constant after an initial period of decline. The value of the regular time Tc is set to a different value for different kinds of light sources (lamps).

The combination characteristic value PC indicates the transmitting efficiency of the quantity of light based on a combination of the light source apparatus (the video processor 30) and the electric scope 10 connected to the video processor 30.

The transmitting efficiency of the quantity of light varies based on a combination of factors that include the condenser optical system of the video processor 30, the shape of the incident end of the light guide 18, the number of the optical fiber, etc.

In the first embodiment, the combination characteristic value PC when the predetermined video processor 30 and the predetermined electric scope 10 are connected to each other is set to 1.

The combination characteristic value PC is set from approximately 0.2 to 6.

The combination characteristic value PC is set every time the electric scope 10 is connected to the video processor 30, and the combination characteristic value PC corresponding to the electric scope 10 that is connected to the video processor 30 is read out from the second memory 32, for calculation purposes.

A large number for the combination characteristic value PC indicates that the transmitting efficiency of the quantity of light from the video processor 30 to the electric scope 10 connected to the video processor 30 is high.

A small number for the combination characteristic value PC indicates that the transmitting efficiency of the quantity of light from the video processor 30 to the electric scope 10 connected to the video processor 30 is low.

In the first embodiment, the combination characteristic value PC is stored in the second memory 32 of the video processor 30; however, the combination characteristic value PC may be stored in the first memory 17 of the electric scope 10. In the case where the combination characteristic value PC is stored in the first memory 17, it is set for every video processor 30 that is connected to the electric scope 10.

The thermal characteristic value PT is a characteristic value of the light source apparatus (the video processor 30) that indicates the effect the light radiated from the video processor 30 has on the temperature of the electric scope 10 as heat.

The setting of the thermal characteristic value PT is based on the spectral characteristics of the light source 36 and the performance of the infrared rays cut filter, etc.

In the first embodiment, a thermal characteristic value PT corresponding to the predetermined kind of video processor 30 is set to 1.

The thermal characteristic value PT is set from approximately 0.5 to 2.

A large number for the thermal characteristic value PT indicates that effect of the radiated light from the video processor 30 on the electric scope 10 is large, so that temperature of the electric scope 10 tends to increase etc.

A small number for the thermal characteristic value PT indicates that the effect of the radiated light from the video processor 30 on the electric scope 10 is small, so that the temperature of the electric scope 10 does not tend to increase etc.

Figure 2:
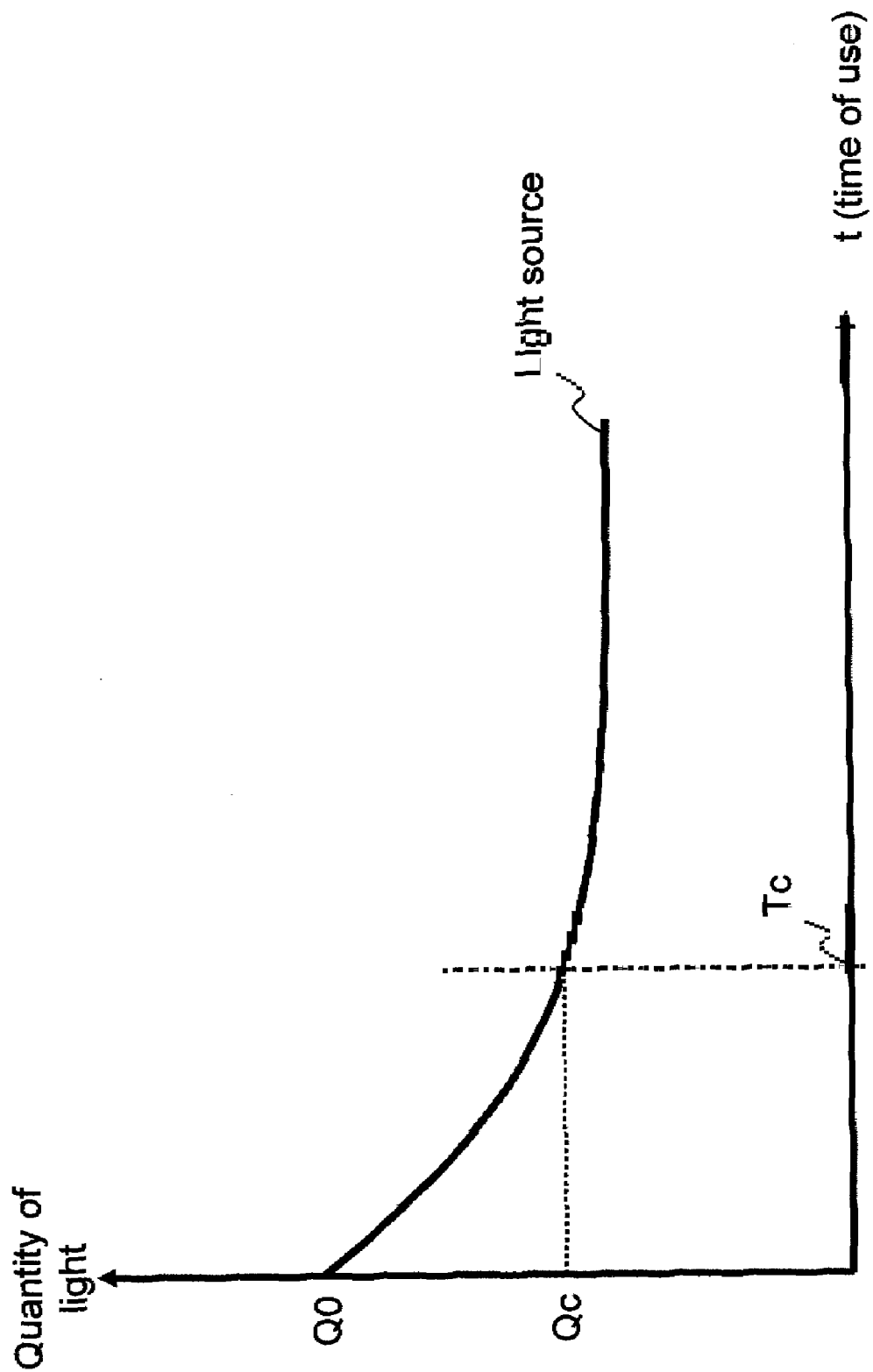
FIG. 2 is a graph that shows a sample of an actual change in the quantity of light radiated from the light source with respect to the time of use.

The quantity of light emitted by the light source 36 decreases linearly with respect to the time of use t until the regular time has elapsed, and then becomes approximately constant thereafter (xenon lamp, see FIG. 2). In the first embodiment, the quantity of light radiated from the light source 36 has an initial light quantity Q0 immediately after the light source 36 is set to the on state, which decreases linearly with respect to the time of use t, and has a constant light quantity Qc after the regular time Tc has elapsed (see FIGS. 3 and 4).

Figure 3:
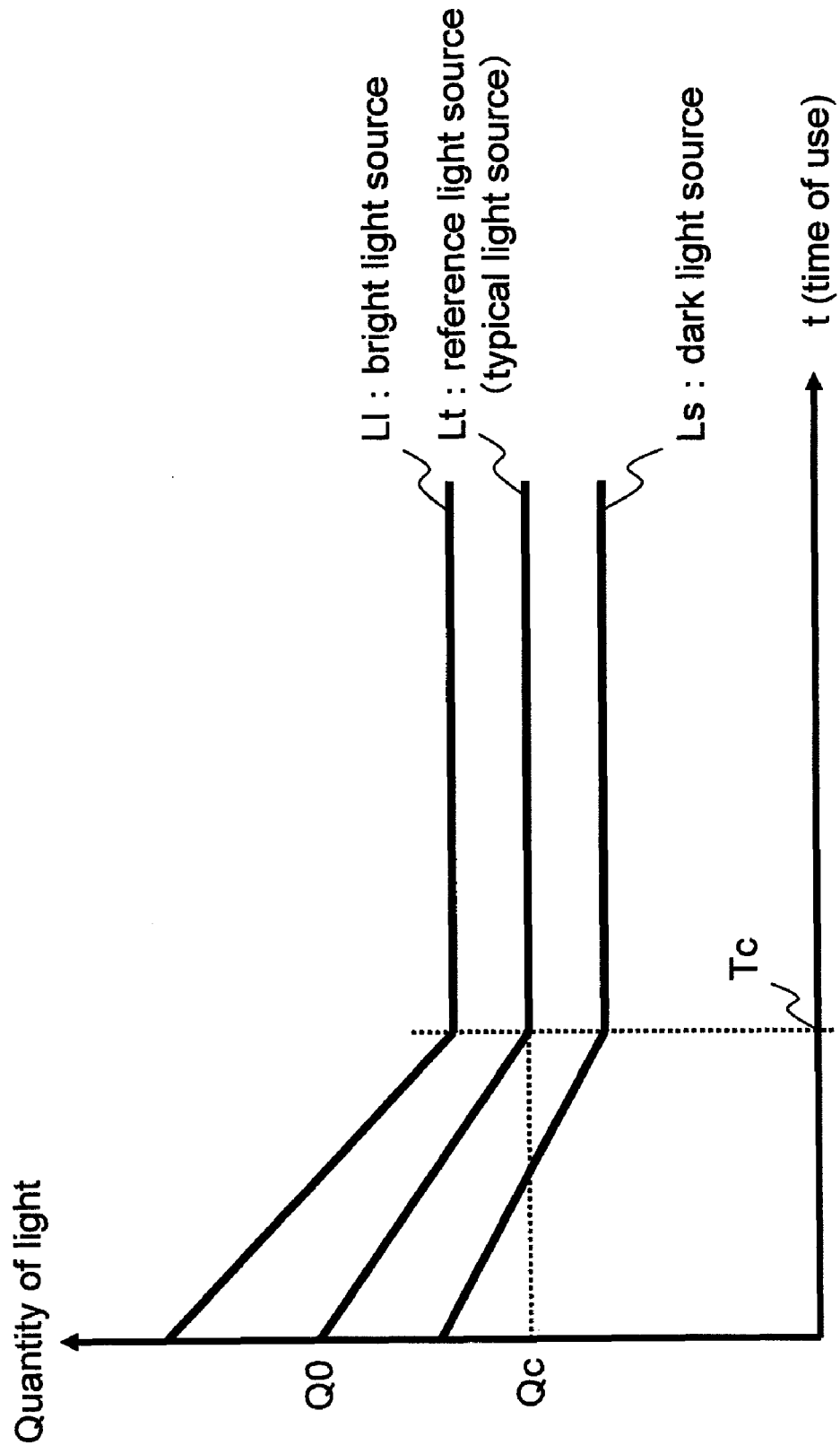
FIG. 3 is a modeled graph that shows a change in the quantity of light radiated light from three different versions of the same light source that vary, corresponding to time.

To illustrate the variability of a light source (lamp), FIG. 3 shows the changes in three different quantities of light, emitted from the same light source, with respect to the time of use t: a large quantity of light Ll, a typical (average) quantity of light Lt, and a small quantity of light Ls.

Figure 4:
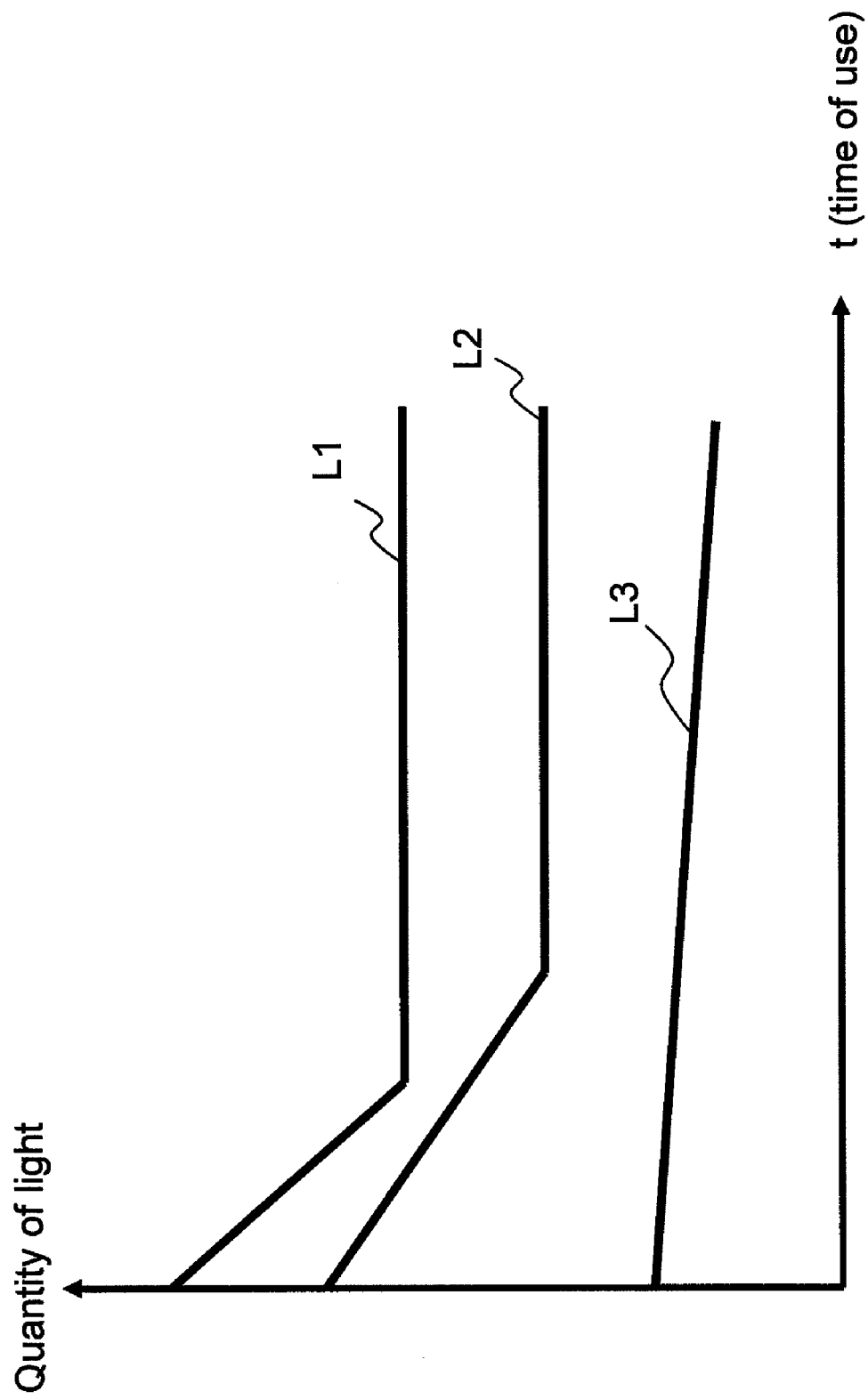
FIG. 4 is a modeled graph that shows a change in the quantity of light radiated from three different light sources with respect to time.

FIG. 4 shows the variations among the quantities of light radiated from different kinds of light sources (a first xenon lamp L1, a second xenon lamp L2, and a halogen lamp L3) with respect to the time of use t.

FIG. 9 shows the light source characteristic value PP, the lamp characteristic value PL, the combination characteristic value PC, the thermal characteristic value PT, and the relative light quantity of the radiated light P corresponding to various kinds of video processors 30 (a first video processor 30A, a second video processor 30B1, and a third video processor 30B2), as an example.

The relative light quantity of the radiated light P as a total characteristics of the light source is a product of the light source characteristic value PP, the lamp characteristic value PL, the combination characteristic value PC, and the thermal characteristic value PT ($P = PP \times PL \times PC \times PT$), and indicates a relative value of the quantity of light incident to the electric scope 10 with respect to the amount of heat transferred to the electric scope 10 and the corresponding increase in temperature of the electric scope 10 due to the transferred heat (a relative value of the total quantity of light radiated from the light source 36 to the electric scope 10).

The second video processor 30B1 and the third video processor 30B2 are the same kind of video processor 30B. The characteristic values for the second video processor 30B1 in the second row of FIG. 9 reflect the condition where the time of use of the light source 36 in the video processor 30B is longer than the regular time Tc. The characteristic values for the third video processor 30B2 in the third row of FIG. 9 reflect the condition immediately after the light source 36 in the video processor 30B is set to the on state.

FIG. 10 shows the scope characteristic value PS and the combination characteristic value PC corresponding to different kinds of electric scopes 10 (a first electric scope 10a, a second electric scope 10b, a third electric scope 10c, a fourth electric scope 10d, a fifth electric scope 10e, and a sixth electric scope 10f), as an example.

The first electric scope 10a and the second electric scope 10b are endoscopes for an upper side alimentary canal EG. The third electric scope 10c and the fourth electric scope 10d are endoscopes for a down side alimentary canal EC. The fifth electric scope 10e and the sixth electric scope 10f are endoscopes for a bronchus EB.

The combination characteristic value PC is set to 1 based on a combination between the video processor 30B and the first electric scope 10a. The combination characteristic value PC corresponding to other combinations between the video processor and the electric scope are based on the combination characteristic value PC between the video processor 30B and the first electric scope 10a (pc=1) which effectively serves as a reference value.

In the first embodiment, when the electric scope 10 is connected to the video processor 30, the second CPU 31 reads out the scope characteristic value PS stored in the first memory 17 through the first CPU 15; makes a comparison between the scope characteristic value PS and the relative light quantity of the radiated light P that is calculated by multiplying the light source characteristic value PP, the lamp characteristic value PL, the combination characteristic value PC, and the thermal characteristic value PT (P=PP×PL×PC× PT); to determine the aperture variable J for setting the optimum aperture degree of the aperture 37.

Therefore, the light control operation is performed in consideration of the characteristics of the electric scope 10 connected to the video processor 30 so that a range of quantities of light is established from which the maximum light quantity can be selected for transmission from the video processor 30 to the electric scope 10 that will effectively mitigate the possibility of either infection caused by the excessive illumination of light through the electric scope 10, or heat-related damage sustained by the incident end of the light guide 18.

The light that is supplied to the electric scope 10 is radiated to the body of the photographing subject. The shutter speed of the electrical shutter of the imaging sensor 11 in the electric scope 10 is adjusted so that the brightness of the image obtained by the endoscope system 1 can be controlled (an auto light control operation).

Figure 5:
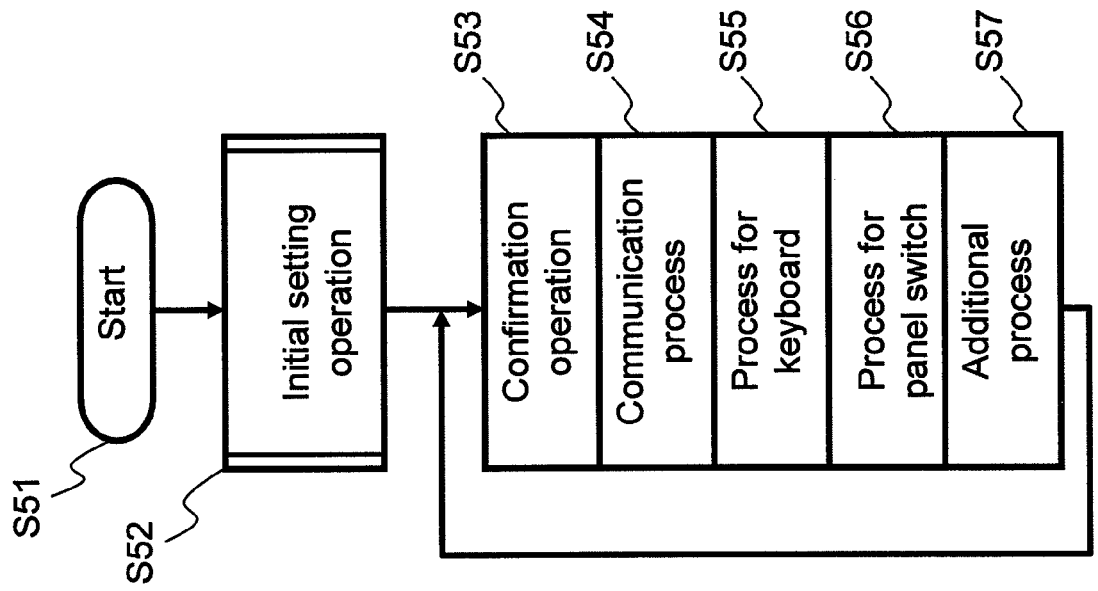
FIG. 5 is a flowchart that shows the contents of the main program of the second CPU.

Next, a process performed by the main program of the second CPU 31 of the video processor 30 is explained by using FIGS. 5 and 6.

In step S51, the main program of the second CPU 31 is started. In step S52, an initial setting operation of the second CPU 31 is performed to initialize the settings for each resister of the second CPU 31 and each resister of the peripheral IC, and to initialize the setting variables.

The second CPU 31 reads the light source characteristic value PP, the lamp characteristic value PL, and the thermal characteristic value PT, all of which correspond to the light source 36 in the video processor 30, from the second memory 32, and then sets these values PP, PL, and PT as variables PP, PL, and PT for calculating the relative light quantity of the radiated light P. Variables PP, PL, and PT are temporarily stored in the RAM of the second CPU 31.

In step S53, a confirmation operation is performed. Specifically, in the confirmation operation, a judgment is made as to whether or not the electric scope 10 is connected to the video processor 30. The detail of the confirmation operation is described later.

In step S54, a communication process with the electric scope 10 is performed. Specifically, in the communication process, transmissions of commands from the electric scope 10 to the video processor 30 and from the video processor 30 to the electric scope 10 are performed.

In step S55, a process corresponding to an input operation to the keyboard 50 is performed.

In step S56, a process corresponding to an input operation for a switch in the panel switch group 43 is performed. For example, supplying power to the light source 36 and adjusting the brightness level of the image displayed on the TV monitor 70 etc. are performed.

In step S57, additional process such as displaying time and date information, etc. are performed.

Next, the confirmation operation in step S53 in FIG. 5 is explained in detail (see FIG. 6).

In step S61, it is determined whether the electric scope 10 has been recently connected to the video processor 30. When it is determined that the electric scope 10 has been recently connected to the video processor 30, the value of variable VS is set to 1 in step S62. The variable VS indicates whether or not the electric scope 10 is connected to the video processor 30. When the electric scope 10 is connected to the video processor 30, the value of the variable VS is set to 1; otherwise, the value of the variable VS is set to 0. The value of the variable VS is temporarily stored in the RAM of the second CPU 31 etc.

Further, the second CPU 31 reads identification data that includes the serial number and name of the electric scope 10, from the electric scope 10.

The second CPU 31 read the scope characteristic value PS from the electric scope 10 in step S62.

In step S63, based on the name read from the electric scope 10, the second CPU 31 reads the combination characteristic value PC, between the video processor 30 and the connected electric scope 10, from the second memory 32 and then sets the value PC as the variable PC for calculating the relative light quantity of the radiated light P. The variable PC is temporarily stored in the RAM of the second CPU 31 etc.

Further, the relative light quantity of the radiated light P is calculated by the second CPU 31.

In step S64, it is determined whether the scope characteristic value PS is smaller or larger than the relative light quantity of the radiated light P.

When the scope characteristic value PS is determined to be smaller than the relative light quantity of the radiated light P, a closing adjustment is made to the aperture degree of the aperture 37, that corresponds to the ratio between the scope characteristic PS and the relative light quantity of the radiated light P. Specifically, the aperture variable J is set to a value equal to 240×(PS÷P), so that the aperture degree is adjusted corresponding to the value of the aperture variable J (J=240× (PS÷P)), in steps S65 and S66.

When it is determined that the scope characteristic value PS is not smaller than the relative light quantity of the radiated light P, an opening adjustment is made to the aperture degree of the aperture 37 (aperture wide open). Specifically, the aperture variable J is set to 240, in steps S67 and S66.

The processes in steps S62 to S67 are performed only when it is determined that the electric scope 10 has been recently connected to the video processor 30.

When it is determined that the electric scope 10 has not been recently connected to the video processor 30 in step S61, it is determined whether the electric scope 10 is disconnected from the video processor 30 in step S68. When it is determined that the electric scope 10 is disconnected from the video processor 30, the value of the variable VS is set to 0.

When it is determined that the electric scope 10 is not disconnected from the video processor 30, the confirmation operation is finished. In other words, when the electric scope 10 neither has been recently connected to the video processor 30, nor is presently disconnected from the video processor 30, no actual operation is performed in the confirmation operation in FIG. 6.

Next, the second embodiment is explained. In the first embodiment, the auto light control operation that controls the brightness of the image obtained by the endoscope system 1 is performed by changing the shutter speed of the electrical shutter of the imaging sensor 11 in the electric scope 10. However, in the second embodiment, the auto light control operation is performed by adjusting the aperture degree of the aperture 37. The points that differ from the first embodiment are explained as follows.

On the basis of a permissible maximum aperture value Jmax and the luminance signal, the second CPU 31 controls the motor 35 that is a stepper motor, changes the aperture degree of the aperture 37, and adjusts the quantity of light incident to the incident end of the light guide 18, in other words, the light radiated to the photographing subject through the light guide 18 is adjustable (the auto light control operation).

By this adjustment of the quantity of light to the incident end of the light guide 18, either the entire amount of light radiated from the light source 36 or a portion thereof can be input to the incident end of the light guide. In the event where less than the entire amount of light radiated from the light source 36 is input to the incident end of the light guide 18, the remaining amount is not input to the incident end of the light guide 18.

In the second embodiment, the shutter speed of the electrical shutter of the imaging sensor 11 is set to a constant value (for example 1/60 second etc.).

In the second embodiment, the value of the aperture variable J that is set in step S65 or S67 in FIG. 6 is used as the permissible maximum aperture value Jmax.

In consideration of the change in the value of the aperture variable J corresponding to time of use, setting the aperture variable J may be performed not only in the confirmation operation of FIG. 6, but may also be performed at another point in time such as when the endoscope system 1 is used after the confirmation operation is complete.

The aperture control is performed under the condition where the aperture variable J is not set higher than the permissible maximum aperture value Jmax in the aperture adjustment based on the luminance signal. In other words the aperture 37 is not opened more than the aperture degree corresponding to the permissible maximum aperture value Jmax.

In the case where the distance between the photographing subject (the observation part) of the body and the tip of the electric scope 10 is great enough to impair so that the brightness of the image obtained by the endoscope system 1, it is one of many situations where the aperture 37 is opened.

In this particular case, when the aperture 37 is opened, the quantity of light incident to the incident end of the light guide 18 is increased so that the quantity of light radiated from the tip of the electric scope 10 increases. Despite the increase in the quantity of radiated light, the possibility of infection caused by the excessive illumination of light from the electric scope 10 remains low due to the relatively long distance separating it from the tip of the electric scope 10. However the increase in the quantity of radiated light in this situation does increase the possibility of the incident end of the light guide sustaining heat-related damage.

In the second embodiment, when the aperture 37 is opened the aperture variable J is not set above the permissible maximum aperture value Jmax in order to prevent the aperture 37 from opening beyond the aperture degree corresponding to the permissible maximum aperture value Jmax. Accordingly, the problem of heat-related damage to the incident end of the light guide 18 is resolved.

Figure 7:
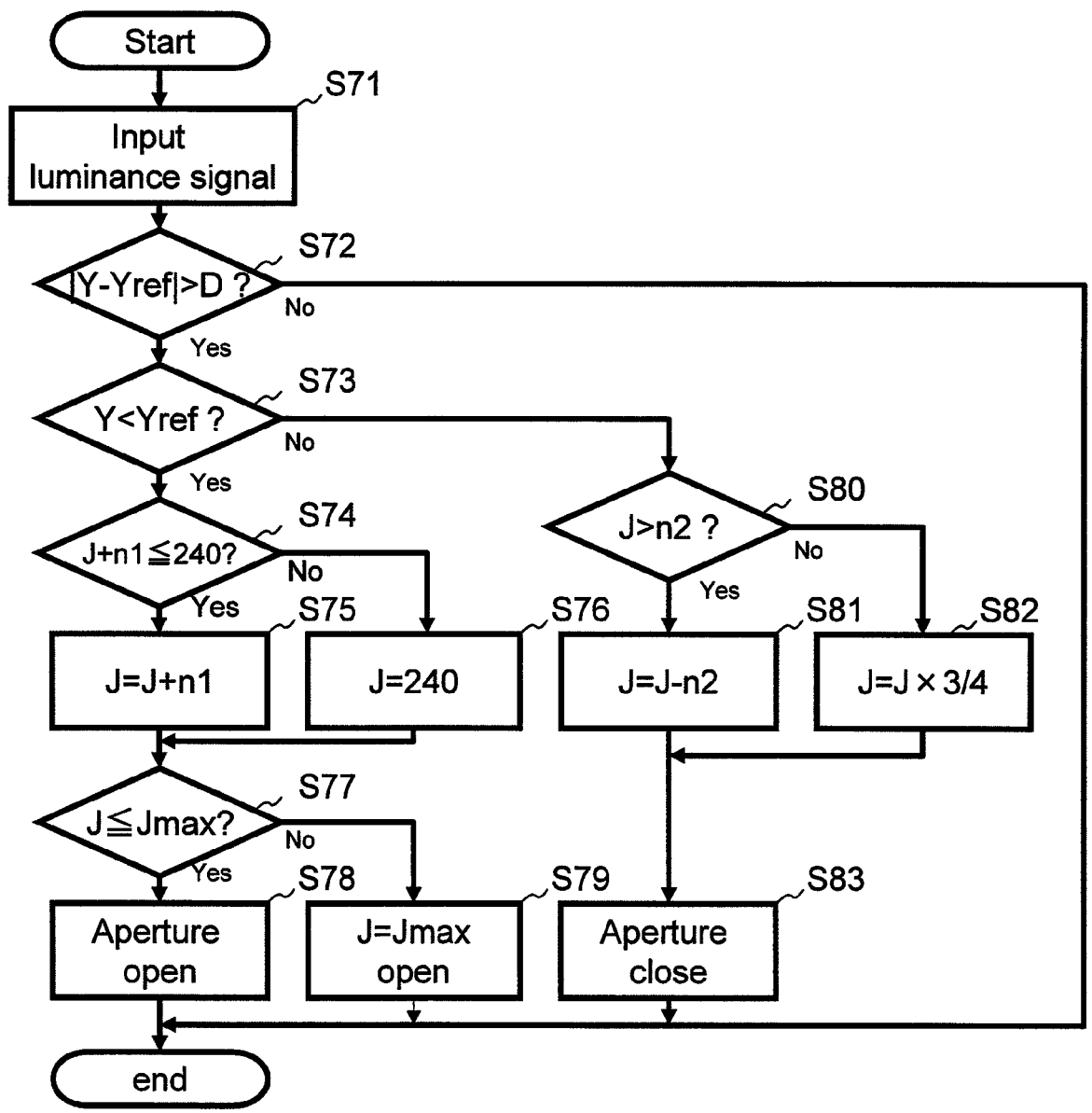
FIG. 7 is a flowchart of the aperture control operation, in detail.

Next, the aperture control operation that is performed as the interruption process is explained by using the flowchart in FIG. 7.

The interruption process is performed for one field, based on a vertical synchronizing signal Vsync output from the signal processing circuit 41.

In step S71, the luminance signal output from the signal processing circuit 41 is input to the second CPU 31 and a luminance variable Y is assigned based on the luminance signal. The luminance variable Y is in the range from 0 (dark) to 255 (bright), corresponding to the brightness of the luminance signal, and is temporarily stored in the RAM of the second CPU 31 etc.

In step S72, a luminance reference value Yref is compared to the value of the luminance variable Y, so that it is determined whether the absolute value of the difference between the luminance reference value Yref and the value of the luminance variable Y exceeds a permissible value D. When it is determined that the absolute value of the difference between the luminance reference value Yref and the value of the luminance variable Y does not exceed the permissible value D, no operation is performed and the aperture control operation is finished.

The luminance reference value Yref is set from 0 (dark) to 255 (bright) in advance of the comparison with the luminance variable Y.

The values of the luminance reference value Yref and the permissible value D are stored in the second memory 32 or the ROM of the second CPU 31. In the second embodiment, the permissible value D is set to 2.

When it is determined that the absolute value of the difference between the luminance reference value Yref and the value of the luminance variable Y is greater than the permissible value D, a determination is then made as to whether the luminance variable Y is smaller than the luminance reference value Yref in step S73. When the luminance variable Y is smaller than the luminance reference value Yref, the situation exists where the image obtained by the endoscope system 1 is dark, and a process to brighten the image obtained by the endoscope system 1 is performed in steps S74 to S79.

In step S74, a determination is made as to whether the sum obtained from adding the aperture variable J to a first value n1 is less than or equal to 240. The first value n1, which is in the range from 1 to 30, is an incremental value used for increasing the aperture variable J. When a small difference exists between the luminance variable Y and the luminance reference value Yref, a small number is assigned to the first value n1; however, when the difference between the luminance variable Y and the luminance reference value Yref is large, a large number is assigned to the first value n1. The first value n1 is stored in the second memory 32 or the ROM of the second CPU 31.

When it is determined that the sum obtained from adding the aperture variable J to the first value n1 is less than or equal to 240, the aperture variable J is set to a new aperture variable J that is the sum of the previous aperture variable J plus the first value n1 (j=j+n1), in step S75.

When it is determined that the sum obtained from adding the aperture variable J to the first value n1 is neither less than nor equal to 240 (greater than 240), the aperture variable J is set to 240 (j=240), in step S76.

In step S77, it is determined whether the aperture variable J is less than or equal to the permissible maximum aperture value Jmax.

When it is determined that the aperture variable J is less than or equal to the permissible maximum aperture value Jmax, the aperture 37 is opened by an amount corresponding to the aperture variable J, in step S78.

When it is determined that the aperture variable J is neither less than nor equal to the permissible maximum aperture value Jmax (greater than the permissible maximum aperture value Jmax), the aperture variable J is set to the permissible maximum aperture value Jmax and the aperture 37 is opened by an amount corresponding to the aperture variable J that is equal to the permissible maximum aperture value Jmax.

Therefore, opening the aperture 37 by an amount greater than the aperture degree corresponding to the permissible maximum aperture value Jmax is prevented.

When it is determined that the luminance variable Y is not less than the luminance reference value Yref in step S73, the situation exists where the image obtained by the endoscope system 1 is bright, and a process to darken the image obtained by the endoscope system 1 dark is performed in steps S80 to S83.

In step S80, a determination is made as to whether the aperture variable j is greater than a second value n2. The second value n2, which is in the range from 1 to 30, is an incremental value used for decreasing the aperture variable J. When a small difference exists between the luminance variable Y and the luminance reference value Yref, a small number is assigned to the second value n2; however, when the difference between the luminance variable Y and the luminance reference value Yref is large, a large number is assigned to the second value n2. The second value n2 is stored in the second memory 32 or the ROM of the second CPU 31.

In step S80, when it is determined that the aperture variable J is not greater than the second value n2, the aperture variable J is set a new aperture variable that is a product of the previous aperture variable J multiplied by ¾ (J=J×¾), in step S82, and the process then continues on to step S83. However, because the aperture variable J is usually greater than the second value n2, the process in step S82 is seldom carried out.

In step S80, when it is determined that the aperture variable J is greater than the second value n2, the aperture variable J is set to a new aperture variable J that is the difference between the previous aperture variable J minus the second value n2 (j=j−n2), in step S81. In step S83, the aperture 37 is closed by an amount corresponding to the aperture variable J.

Next, the third embodiment is explained. In the first embodiment, the auto light control operation that controls the brightness of the image obtained by the endoscope system 1 is performed by changing the shutter speed of the electrical shutter of the imaging sensor 11 in the electric scope 10. In the second embodiment, the auto light control operation is performed by adjusting the aperture degree of the aperture 37. However, in the third embodiment, the light control operation is performed manually. The points that differ from the first and second embodiments are explained as follows.

The manual light control operation is performed by operating a brightness-up switch and a brightness-down switch in the panel switch group 43.

In the third embodiment, 10 different levels of a brightness can be selected by using the brightness-up switch and the brightness-down switch.

A light quantity ratio corresponding to the brightness of level 10 (a maximum value) is set to 1. Based on this combination, the light quantity ratios corresponding to the brightness of levels 1 to 9 are set accordingly so that the aperture variable J corresponds to the light quantity ratio (see FIG. 11). The table maintaining the relationship data between the brightness level, the light quantity ratio, and the aperture variable J that is shown in FIG. 11, is stored in the ROM of the second CPU 31.

In the third embodiment, the process of the main program that is shown in FIG. 5, is performed. The adjustment of the brightness level is performed in the process corresponding to the input operation to the switch in the panel switch group 43, which is shown in step S56 of FIG. 5.

Figure 8:
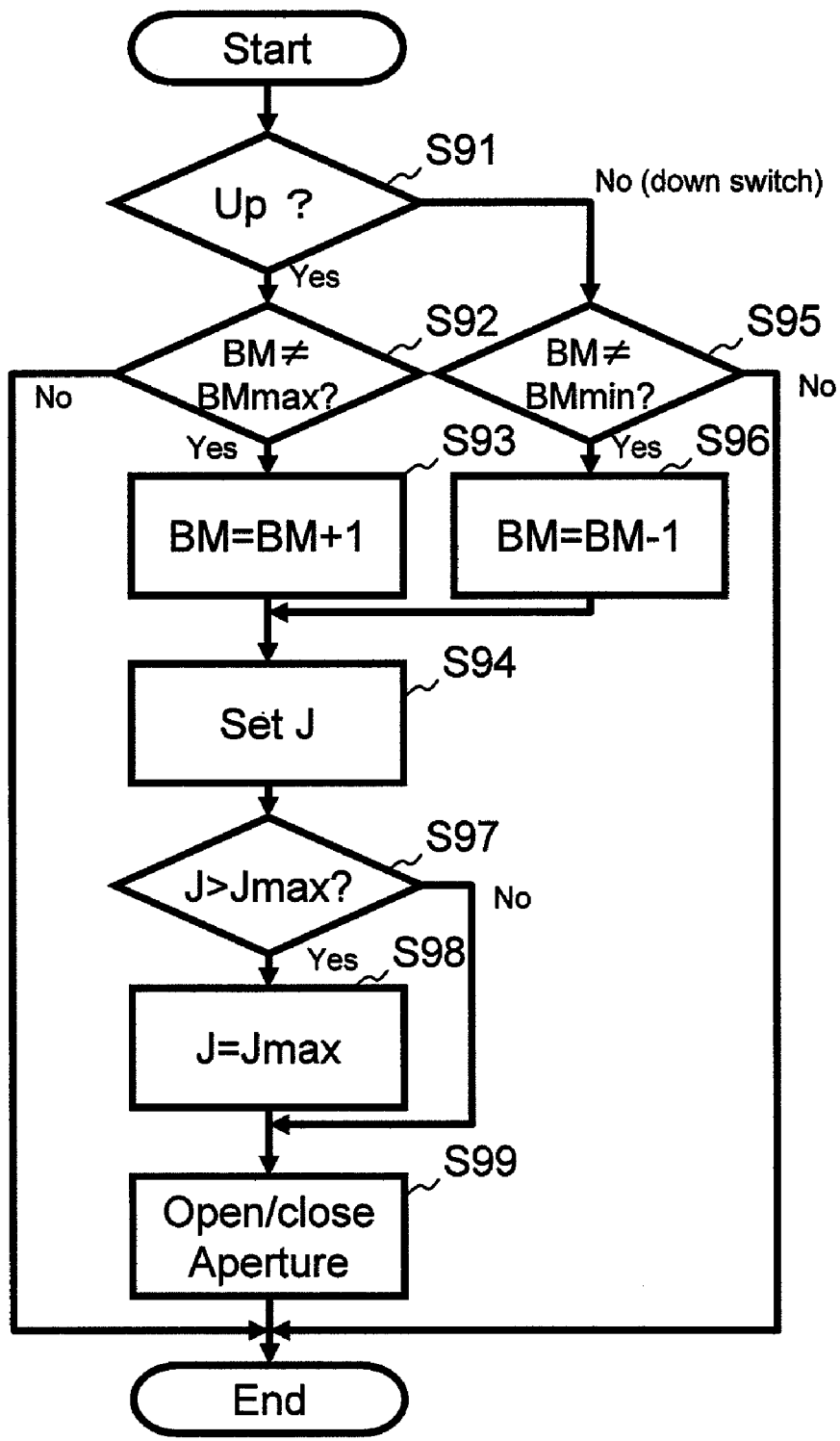
FIG. 8 is a flowchart of the adjustment of the brightness level, in detail.

Next, the detail of the adjustment of the brightness level is explained by using the flowchart in FIG. 8.

When one of either the brightness-up switch or the brightness-down switch is operated, it is determined whether the brightness-up switch is operated in step S91. When it is determined that the brightness-up switch is operated, the process continues on to step S92. When it is determined that the brightness-up switch is not operated (the brightness-down switch is operated), the process is forwarded to step S95.

In Step S92, it is determined whether the brightness level is set to the maximum value (=10). Specifically, it is determined whether a brightness variable BM is equal to a brightness maximum value BMmax (=10).

The brightness variable BM indicates the brightness level of the light incident to the incident end of the light guide 18, and is set in the range from 1 to 10.

When the brightness variable BM is 10, the brightness level does not rise compared to the present brightness level, and the process of adjusting the brightness level is complete without any further operation.

When the brightness variable BM is not 10, the value of the brightness variable BM is increased by the value of 1 (BM=BM+1), in step S93. In step S94, the value of the aperture variable J corresponding to the modified brightness variable BM is updated based on the table in FIG. 11 stored in the ROM of the second CPU 31.

In Step S95, it is determined whether the brightness level is set to the minimum value (=1). Specifically, it is determined whether the brightness variable BM is equal to a brightness minimum value BMmin (=1).

When the brightness variable BM is 1, the brightness level does not fall compared to the present brightness level, and the process of adjusting the brightness level is complete without any further operation.

When the brightness variable BM is not 1, the value of the brightness variable BM is reduced by the value of 1 (BM=BM−1), in step S96. In step S94, the value of the aperture variable J corresponding to the modified brightness variable BM is updated based on the table in FIG. 11 stored in the ROM of the second CPU 31.

In step S97, it is determined whether the aperture variable J is greater than the permissible maximum aperture value Jmax.

When it is determined that the aperture variable J is greater than the permissible maximum aperture value Jmax, the aperture variable J is set to a value that is equal to the permissible maximum aperture value Jmax, in step 98. In step S99, the aperture degree of the aperture 37 is set in accordance to the aperture variable J that is equal to the permissible maximum aperture value Jmax.

When it is determined that the aperture variable J is not greater than the permissible maximum aperture value Jmax, the aperture degree of the aperture 37 is set in accordance to the aperture variable J that is less than or equal to the permissible maximum aperture value Jmax, in step S99, without proceeding to step S98.

Therefore, the aperture 37 can be prevented from opening by an amount that is greater than the aperture degree corresponding to the permissible maximum aperture value Jmax.

In the first, second, and third embodiments, the light control operation for adjusting the aperture degree of the aperture 37 is explained.

However, the light control operation may be performed by adjusting quantity of electric current that is supplied to the light source 36.

In this case, the same light control operation can be performed in the first, second, and third embodiments, by replacing the aperture variable J with a variable that represents a quantity Q of radiated light corresponding to a quantity C of electric current that is supplied to the light source 36.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2006-124129 (filed on Apr. 27, 2006) which is expressly incorporated herein by reference, in its entirety.

The invention claimed is:

1. An endoscope system comprising:
an electric scope comprising a light guide; and
a light source apparatus that has a light source and a light control apparatus;
said light control apparatus adjusting a quantity of light that is incident to said electric scope, based on a comparison between a scope characteristic that indicates a relative value of the maximum quantity of light permitted to be incident to said electric scope from said light source, and a light source total characteristic that indicates a relative value of the quantity of the light radiated from said light source to said electric scope, said light source total characteristic being a calculated value that is independent of an object viewed by the electric scope,
wherein the scope characteristic is set to a value so as to prevent at least one of damage to an incident end of the light guide, and infection due to excessive light illumination,
said light source total characteristic is a product of a lamp characteristic, a combination characteristic, and a thermal characteristic,
said lamp characteristic indicates a change in the quantity of light emitted from said light source during a time of use and indicates the variability in the quantity of radiated light among the same kind of said light source;
said combination characteristic indicates a transmitting efficiency of the quantity of light based on a combination of said light source apparatus and said electric scope connected to said light source apparatus; and
said thermal characteristic indicates the degree to which the effect the light radiated from said light source apparatus influences the temperature of said electric scope as heat.

2. The endoscope system according to claim 1, wherein said light source total characteristic is also based on a light source characteristic, and
said light source characteristic indicates a relative quantity of light radiated from each different kind of said light source.

3. The endoscope system according to claim 1, wherein said combination characteristic is stored in said light source apparatus for every said electric scope connected to said light source apparatus.

4. The endoscope system according to claim 1, wherein said lamp characteristic changes corresponding to the time of use.

5. The endoscope system according to claim 1, wherein said scope characteristic is stored in said electric scope, and is read out when said electric scope is connected to said light source apparatus; and
said light source total characteristic is stored in said light source apparatus.

6. The endoscope system according to claim 1, wherein said scope characteristic and said light source total characteristic are stored in said light source apparatus.

7. The endoscope system according to claim 1, wherein said light control apparatus adjusts a maximum value of said quantity of light that is incident to said electric scope corresponding to a ratio between said scope characteristic and said light source total characteristic, when said scope characteristic is less than said light source total characteristic.

8. The endoscope system according to claim 7, wherein said light control apparatus adjusts said maximum value corresponding to said ratio by adjusting an aperture degree of an aperture.

9. The endoscope system according to claim 8, wherein a brightness of an image that is obtained by said endoscope system is controlled by changing a shutter speed of an electrical shutter of an imaging sensor in said electric scope.

10. The endoscope system according to claim 8, wherein a brightness of an image that is obtained by said endoscope system is controlled by adjusting said aperture degree of said aperture, under the condition where said aperture is not opened by an amount in excess of the aperture degree corresponding to said maximum value of said quantity of light that is incident to said electric scope, based on a luminance signal of said image.

11. The endoscope system according to claim 8, wherein a brightness of an image that is obtained by said endoscope system is manually controlled by adjusting said aperture degree of said aperture, under the condition where said aperture is not opened by an amount in excess of the aperture degree corresponding to said maximum value of said quantity of light that is incident to said electric scope.

12. The endoscope system according to claim 7, wherein said light control apparatus adjusts corresponding to said ratio, by adjusting quantity of electric current that is supplied to said light source.

* * * * *